United States Patent [19]
Senn-Bilfinger

[11] Patent Number: 6,160,119
[45] Date of Patent: Dec. 12, 2000

[54] FUSED DIHYDROPYRANS

[75] Inventor: Jörg Senn-Bilfinger, Constance, Germany

[73] Assignee: Byk Gulden Lomberg Chemische Fabrik GmbH, Constance, Germany

[21] Appl. No.: 09/423,626

[22] PCT Filed: May 23, 1998

[86] PCT No.: PCT/EP98/03057

§ 371 Date: Nov. 16, 1999

§ 102(e) Date: Nov. 16, 1999

[87] PCT Pub. No.: WO98/54188

PCT Pub. Date: Dec. 3, 1998

[30] Foreign Application Priority Data

May 28, 1997 [EP] European Pat. Off. .............. 97108574

[51] Int. Cl.[7] .................... A61K 31/435; C07D 491/147; C07D 491/22
[52] U.S. Cl. .............................. 546/83; 514/293; 546/65; 546/83
[58] Field of Search ........................ 546/83, 65; 514/293, 514/287

[56] References Cited

U.S. PATENT DOCUMENTS 4,468,400  8/1984  Gold et al. .............................. 424/256

*Primary Examiner*—Bernard Dentz
*Attorney, Agent, or Firm*—Jacobson, Price, Holman & Stern, PLLC

[57] ABSTRACT

Compounds of formula (I) in which the substituents have the meanings mentioned in the specification, are suitable for the prevention and treatment of gastrointestinal diseases.

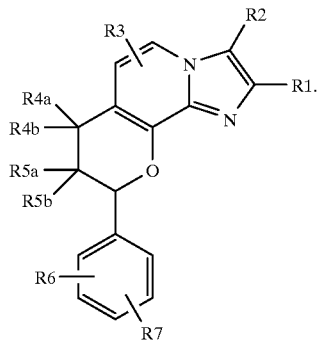

10 Claims, No Drawings

FUSED DIHYDROPYRANS

This is a 371 of PCT/EP99/03057 filed May 23, 1998.

FIELD OF APPLICATION OF THE INVENTION

The invention relates to novel compounds which are used in the pharmaceutical industry as active compounds for the production of medicaments.

KNOWN TECHNICAL BACKGROUND

U.S. Pat. No. 4,468,400 describes tricyclic imidazo[1,2-a]pyridines having various ring systems fused onto the imidazopyridine parent structure, which should be suitable for the treatment of peptic ulcer disorders. The International Patent Application WO 95/27714 describes 8,9-dihydropyrano[2,3-c]imidazo[1,2-a]pyridines having gastric acid secretion-inhibiting properties.

DESCRIPTION OF THE INVENTION

It has now been found that the compounds described below in greater detail, which differ from the compounds of the prior art, in particular by the substitution in the 7- and/or 8-position of the 8,9-dihydropyrano[2,3-c]imidazo[2-a]pyridine, have particularly advantageous properties.

The invention relates to compounds of the formula I

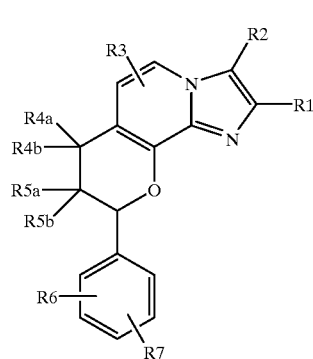

(I)

in which $R_1$ is 1-4C-alkyl, $R_2$ is 1-4C-alkyl or hydroxy 1-4C-alkyl, $R_3$ is hydrogen or halogen, one of the substituents $R_4a$ and $R_4b$ is hydrogen and the other is hydrogen, hydroxyl, 1-4C-alkoxy, 1-4C-alkoxy-1-4C-alkoxy or 1-4C-alkylcarbonyloxy, or in which $R_4a$ and $R_4b$ together are O (oxygen), one of the substituents $R_5a$ and $R_5b$ is hydrogen and the other is hydrogen, hydroxyl, 1-4C-alkoxy, 1-4C-alkoxy-1-4C-alkoxy or 1-4C-alkylcarbonyloxy, or in which $R_5a$ and $R_5b$ together are O (oxygen), where $R_4a$, $R_4b$, $R_5a$ and $R_5b$ are not simultaneously hydrogen, or in which one of the substituents $R_4a$ and $R_4b$ on the one hand and one of the substituents $R_5a$ and $R_5b$ on the other hand is in each case hydrogen, and the other substituents in each case together form a methylenedioxy radical (—O—CH2—O—) or an ethylenedioxy radical (—O—CH$_2$—CH$_2$—O—), $R_6$ is hydrogen, halogen, 1-4C-alkyl, 1-4C-alkoxy, 1-4C-alkoxycarbonylamino, 1-4C-alkoxy-1-4C-alkoxycarbonylamino or trifluoromethyl and $R_7$ is hydrogen, halogen, 1-4C-alkyl or 1-4C-alkoxy, and their salts.

1-4C-alkyl represents straight-chain or branched alkyl radicals having 1 to 4 carbon atoms. Examples which may be mentioned are the butyl radical, isobutyl radical, sec-butyl radical, tert-butyl radical, propyl radical, isopropyl radical, ethyl radical and the methyl radical. The methyl radical is preferred.

Hydroxy-1-4C-alkyl represents abovementioned 1-4C-alkyl radicals which are substituted by a hydroxyl group. Examples which may be mentioned are the hydroxymethyl radical, the 2-hydroxyethyl radical and the 3-hydroxypropyl radical. The hydroxymethyl radical is preferred.

Halogen in the sense of the invention is bromine, chlorine or fluorine.

1-4C-alkoxy represents radicals which, in addition to the oxygen atom, contain a straight-chain or branched alkyl radical having 1 to 4 carbon atoms. Examples which may be mentioned are the butoxy radical, isobutoxy radical, sec-butoxy radical, tert-butoxy radical, propoxy radical, isopropoxy radical and preferably the ethoxy radical and methoxy radical.

1-4C-alkoxy-1-4C-alkoxy represents one of the abovementioned 1-4C-alkoxy radicals which is substituted by a further 1-4C-alkoxy radical. Examples which may be mentioned are the radicals 2-(methoxy)ethoxy (CH$_3$—O—CH$_2$—CH$_2$—O—) and 2-(ethoxy)ethoxy (CH$_3$—CH$_2$—O—CH$_2$—CH$_2$—O—).

1-4C-alkylcarbonyloxy represents a carbonyloxy group to which is bonded one of the abovementioned 1-4C-alkyl radicals. An example which may be mentioned is the acetoxy radical (CH$_3$CO—O—).

1-4C-alkoxycarbonyl represents a carbonyl group to which is bonded one of the abovementioned 1-4C-alkoxy radicals. Examples which may be mentioned are the methoxycarbonyl radical (CH$_3$O—C(O)—) and the ethoxycarbonyl radical (CH$_3$CH$_2$O—C(O)—).

1-4C-alkoxycarbonylamino represents an amino radical which is substituted by one of the abovementioned 1-4C-alkoxycarbonyl radicals. Examples which may be mentioned are the ethoxycarbonylamino radical and the methoxycarbonylamino radical.

1-4C-alkoxy-1-4C-alkoxycarbonyl represents a carbonyl group to which is bonded one of the abovementioned 1-4C-alkoxy-1-4C-alkoxy radicals. Examples which may be mentioned are the 2-(methoxy)ethoxycarbonyl radical (CH$_3$—O—CH$_2$CH$_2$—O—CO—) and the 2-(ethoxy)ethoxycarbonyl radical (CH$_3$CH$_2$—O—CH$_2$CH$_2$—O—CO—).

1-4C-alkoxy-1-4C-alkoxycarbonylamino represents an amino radical which is substituted by one of the abovementioned 1-4C-alkoxy-1-4C-alkoxycarbonyl radicals. Examples which may be mentioned are the 2-(methoxy)ethoxycarbonylamino radical and the 2-(ethoxy)ethoxycarbonylamino radical.

Suitable salts of compounds of the formula I—depending on substitution—are especially all acid addition salts. Particular mention may be made of the pharmacologically tolerable salts of the inorganic and organic acids customarily used in pharmacy. Those suitable are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)-benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in salt preparation—depending on whether a mono- or polybasic acid is concerned and depending on which salt is desired—in an equimolar quantitative ratio or one differing therefrom.

Pharmacologically intolerable salts which can be initially obtained as process products, for example in the preparation of the compounds according to the invention on an industrial scale, are converted into pharmacologically tolerable salts by processes known to the person skilled in the art.

According to expert's knowledge the compounds of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

The compounds of the formula I have three chiral centers. The invention relates to all eight conceivable stereoisomers in any desired mixing ratio with one another, including the pure enantiomers, which are a preferred subject of the invention.

If one of the substituents $R_4a$ and $R_4b$ on the one hand and one of the substituents $R_5a$ and $R_5b$ on the other hand together form a methylenedioxy radical or ethylenedioxy radical, the two substituents which form the methylenedioxy radical or ethylenedioxy radical are-preferably cis to one another.

Compounds to be emphasized are those of the formula I, in which $R_1$ is 1-4C-alkyl, $R_2$ is 1-4C-alkyl or hydroxy-1-4C-alkyl, $R_3$ is hydrogen, one of the substituents $R_4a$ and $R_4b$ is hydrogen and the other is hydrogen, hydroxyl or 1-4C-alkoxy, or in which $R_4a$ and $R_4b$ together are O (oxygen), one of the substituents $R_5a$ and $R_5b$ is hydrogen and the other is hydrogen, hydroxyl or 1-4C-alkoxy, or in which $R_5a$ and $R_5b$ together are O (oxygen), where $R_4a$, $R_4b$, $R_5a$ and $R_5b$ are not simultaneously hydrogen, $R_6$ is hydrogen, halogen or trifluoromethyl and $R_7$ is hydrogen or halogen, and their salts.

An embodiment of the invention to be emphasized are compounds of the formula I*

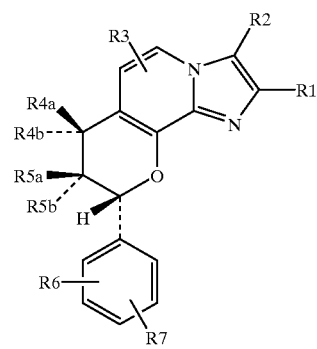

in which $R_1$ is 1-4C-alkyl, $R_2$ is 1-4C-alkyl or hydroxy-1-4C-alkyl, $R_3$ is hydrogen, one of the substituents $R_4a$ and $R_4b$ is hydrogen and the other is hydrogen, hydroxyl or 1-4C-alkoxy, one of the substituents $R_5a$ and $R_5b$ is hydrogen and the other Is hydrogen, hydroxyl or 1-4C-alkoxy, where $R_4a$, $R_4b$, $R_5a$ and $R_5b$ are not simultaneously hydrogen, $R_6$ Is hydrogen, halogen or trifluoromethyl and $R_7$ is hydrogen or halogen, and their salts.

An embodiment of the invention particularly to be emphasized are compounds of the formula I*, in which $R_1$ is 1-4C-alkyl, $R_2$ is 1-4C-alkyl or hydroxymethyl, $R_3$ is hydrogen, $R_4a$ is hydrogen, $R_4b$ is hydroxyl or 1-4C-alkoxy, $R_5a$ is hydrogen, hydroxyl or I-4C-alkoxy, $R_5b$ is hydrogen, $R_6$ is hydrogen, halogen or trifluoromethyl and $R_7$ is hydrogen or halogen, and their salts.

A preferred embodiment of the invention are compounds of the formula I*, in which $R_1$ is 1-4C-alkyl, $R_2$ is 1-4C-alkyl, $R_3$ is hydrogen, $R_4a$ is hydrogen, $R_4b$ is hydroxyl, $R_5a$ is hydroxyl, $R_5b$ is hydrogen, $R_6$ is hydrogen, halogen or trifluoromethyl and $R_7$ is hydrogen or halogen, and their salts.

With the aid of the general formula I*, the following exemplary compounds according to the invention may actually be mentioned by means of the substituent meanings and by the positions indicated for the substituents $R_3$, $R_6$ and $R_7$ in the following Table 1 (Tab. 1):

TABLE 1

(I*)

| R1 | R2 | R3 | R4a | R4b | R5a | R5b | R6 | R7 |
|---|---|---|---|---|---|---|---|---|
| $CH_3$ | CH3 | H | O | | H | H | H | H |
| $CH_3$ | CH3 | H | H | OH | H | H | H | H |
| $CH_3$ | CH3 | H | O | | H | H | 2-Cl | H |
| $CH_3$ | CH3 | H | H | OH | H | H | 2-Cl | H |
| $CH_3$ | $CH_3$ | H | O | | H | H | 2-Cl | 6-Cl |
| $CH_3$ | $CH_3$ | H | H | OH | H | H | 2-Cl | 6-Cl |
| $CH_3$ | $CH_3$ | H | H | $OCH_3$ | H | H | H | H |
| $CH_3$ | $CH_3$ | H | H | $OC_2H_5$ | H | H | H | H |
| $CH_3$ | $CH_3$ | H | O | | H | H | $2-CF_3$ | H |
| $CH_3$ | $CH_3$ | H | H | OH | H | H | $2-CF_3$ | H |
| $CH_3$ | $CH_3$ | H | O | | OH | H | H | H |
| $CH_3$ | $CH_3$ | H | H | OH | OH | H | H | H |
| $CH_3$ | $CH_3$ | 6-Br | O | | H | H | H | H |
| $CH_3$ | $CH_3$ | 6-Br | H | OH | H | H | H | H |
| $CH_3$ | $CH_3$ | 6-Cl | H | OH | H | H | H | H |
| $CH_3$ | $CH_3$ | 6-Cl | H | OH | OH | H | H | H |
| $CH_3$ | $CH_3$ | H | H | OH | OH | H | 2-Cl | H |
| $CH_3$ | $CH_3$ | H | H | OH | OH | H | 2-Cl | 6-Cl |
| $CH_3$ | $CH_3$ | H | H | OH | OH | H | 4-C | H |
| $CH_3$ | $CH_3$ | H | H | OH | OH | H | $2-CF_3$ | H |
| $CH_3$ | $CH_3$ | H | H | OH | OH | H | 2-NHCO—$OCH_3$ | 6-$CH_3$ |
| $CH_3$ | $CH_3$ | H | H | OH | OH | H | 2-NHCO—$OC_2H_4$—$OCH_3$ | 6-$CH_3$ |
| $CH_3$ | $CH_2OH$ | H | O | | H | H | H | H |
| $CH_3$ | $CH_2OH$ | H | H | OH | H | H | H | H |
| $CH_3$ | $CH_2OH$ | H | O | | H | H | 2-Cl | H |
| $CH_3$ | $CH_2OH$ | H | H | OH | H | H | 2-Cl | H |
| $CH_3$ | $CH_2OH$ | H | O | | H | H | 2-Cl | 6-Cl |
| $CH_3$ | $CH_2OH$ | H | H | OH | H | H | 2-Cl | 6-Cl |
| $CH_3$ | $CH_2OH$ | H | H | $OCH_3$ | H | H | H | H |
| $CH_3$ | $CH_2OH$ | H | H | $OC_2H_5$ | H | H | H | H |
| $CH_3$ | $CH_2OH$ | H | O | | H | H | $2-CF_3$ | H |
| $CH_3$ | $CH_2OH$ | H | H | OH | H | H | $2-CF_3$ | H |
| $CH_3$ | $CH_2OH$ | H | O | | OH | H | H | H |
| $CH_3$ | $CH_2OH$ | H | H | OH | OH | H | H | H |
| $CH_3$ | $CH_2OH$ | 6-Br | O | | H | H | H | H |
| $CH_3$ | $CH_2OH$ | 6-Br | H | OH | H | H | H | H |
| $CH_3$ | $CH_2OH$ | 6-Cl | H | OH | H | H | H | H |
| $CH_3$ | $CH_2OH$ | 6-Cl | H | OH | OH | H | H | H |
| $CH_3$ | $CH_2OH$ | H | H | OH | OH | H | 2-Cl | H |
| $CH_3$ | $CH_2OH$ | H | H | OH | OH | H | 2-Cl | 6-Cl |
| $CH_3$ | $CH_2OH$ | H | H | OH | OH | H | 4-Cl | H |
| $CH_3$ | $CH_2OH$ | H | H | OH | OH | H | $2-CF_3$ | H |
| $CH_3$ | $CH_2OH$ | H | H | OH | OH | H | 2-NHCO—$OCH_3$ | 6-$CH_3$ |
| $CH_3$ | $CH_2OH$ | H | H | OH | OH | H | 2-NHCO—$OC_2H_4$—$OCH_3$ | 6-$CH_3$ | and the salts of the compounds mentioned in Table 1, the character "O" (=oxygen) between $R_4a$ und $R_4b$ in Table 1 denoting a 7-oxo compound.

The compounds according to the invention can thus be prepared as described by way of example in the following examples, or using analogous process steps starting from appropriate starting compounds.

The starting compounds are known or can be prepared analogously to the known compounds.

Depending on the substitution pattern in positions 7 and 8 ($R_4a/R_4b$ or $R_5a/R_5b$), the compounds according to the invention can be prepared starting from 8-hydroxyimidazo [2-a]pyridines which are known or can be prepared in a known manner (see, for example, WO 95/27714) according to the following reaction schemes:

Scheme 1

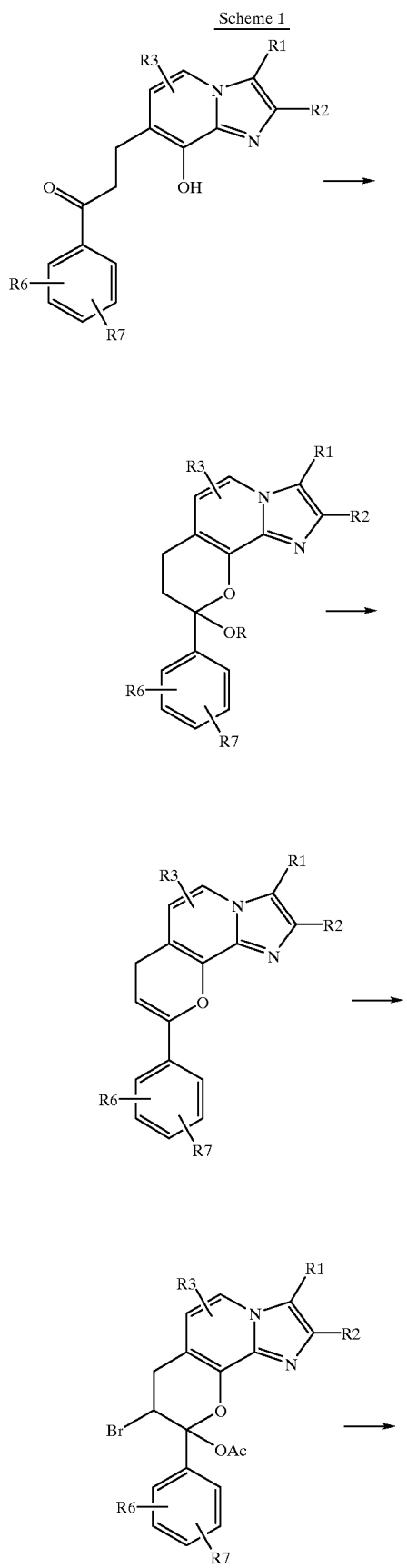

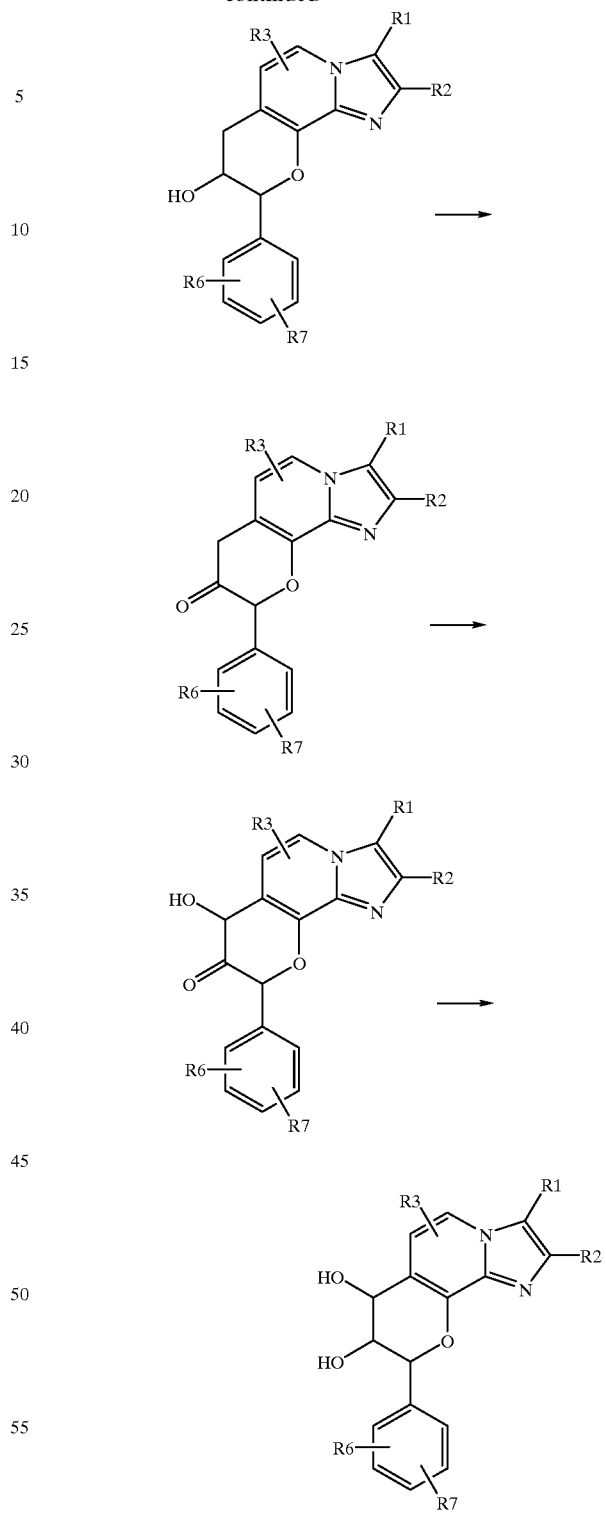

The 8-hydroxyimidazo[2-a]pyridine substituted in the 7-position is converted to the cyclic acetal. After elimination to give the pyrano[2,3-c]imidazo[2-a]pyridine, bromine and acetoxy are added (e.g. by treating with glacial acetic acid/acetic anhydride and N-bromosuccinimide) and it is reductively hydrolyzed to the 8-hydroxy compound. The selective oxidation which follows if desired leads via the 8-keto compound to the 7-hydroxy-8-keto compound, which for its part can also be converted into the 7,8-dihydroxy compound by reduction of the keto group, for example using sodium borohydride.

Scheme 2

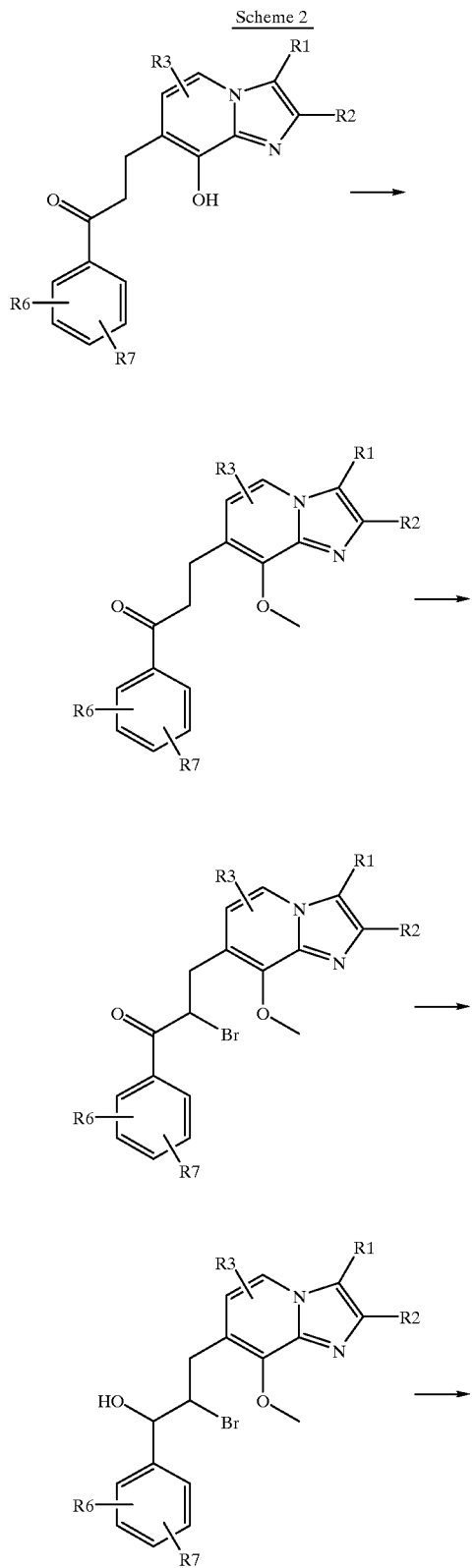

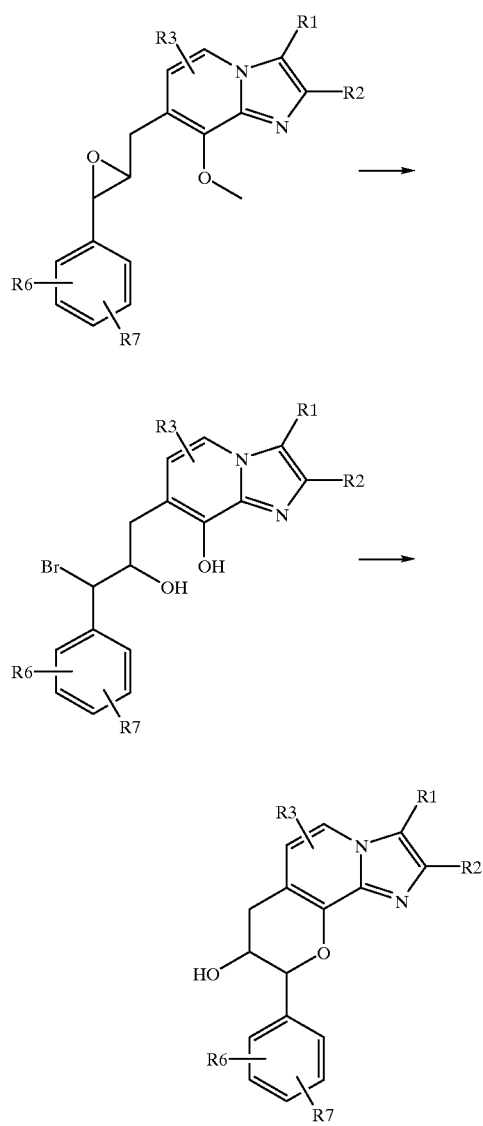

The starting material known from Scheme 1 is O-methylated, brominated in the α-position to give the keto group, for example by means of bromine in trichloromethane, then reduced to the bromohydrin and converted into the corresponding epoxide. By treatment with HBr, the 8-deprotected inverse bromohydrin is obtained, which spontaneously cyclizes to the desired target compound.

Scheme 3

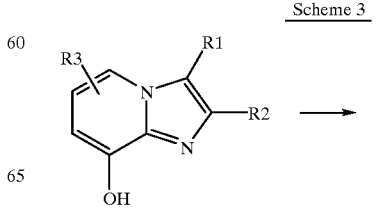

-continued

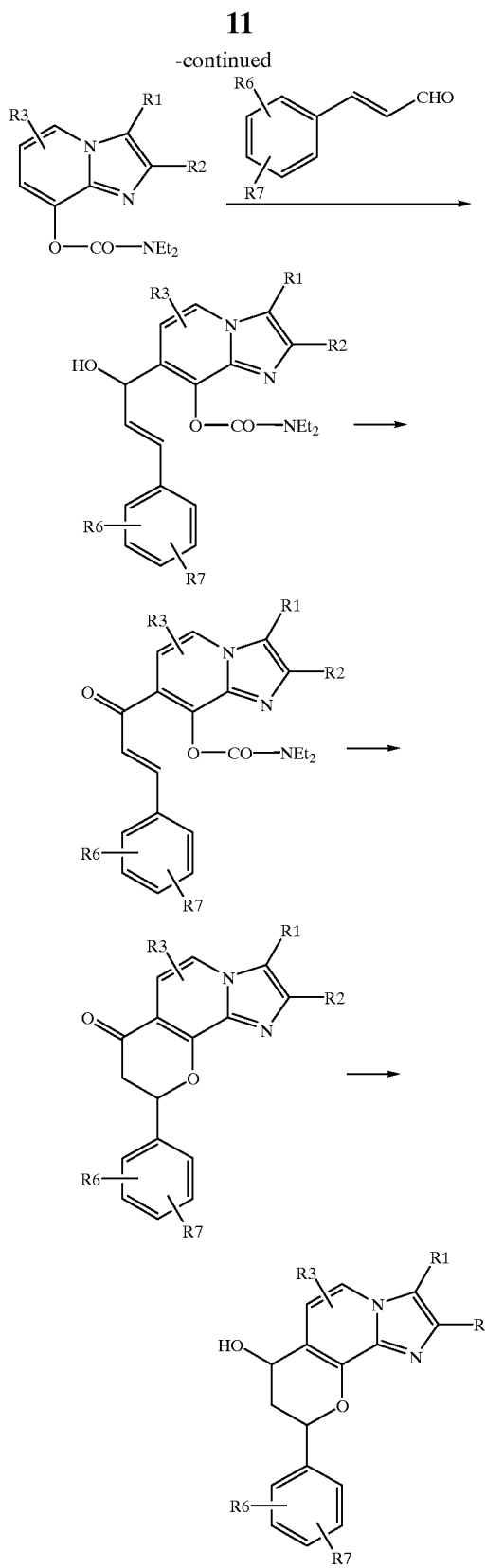

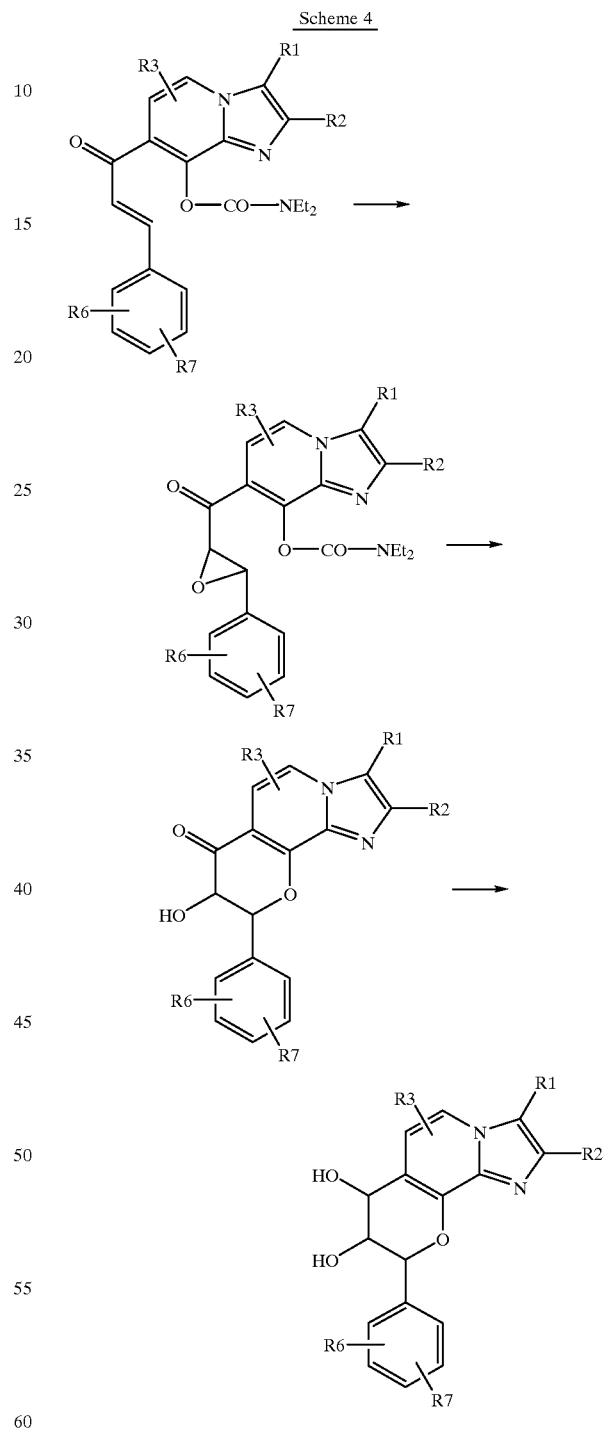

known from the literature. The addition product obtained is oxidized (e.g. with manganese dioxide), cyclized under strongly acidic conditions with removal of the protective group and, if desired, reduced to the alcohol by means of sodium borohydride.

The hydroxyl group of the 8-hydroxyimidazo[1,2-a] pyridine is first converted into an 8-diethylaminocarbonyloxy group. This protected imidazo [1,2-a]pyridine deprotonated in the 7-position, for example, by t-butyllithium is then reacted with a cinnamaldehyde The 7-cinnamoyl derivative known from Scheme 3 is first epoxidized using a suitable oxidant, such as, for example, hydrogen peroxide. The removal of the protective group and the ring closure is then carried out under acidic or basic conditions. The reduction of the keto group which then follows if desired can in turn be carried out—analogously to the process for Scheme 1—for example using sodium borohydride.

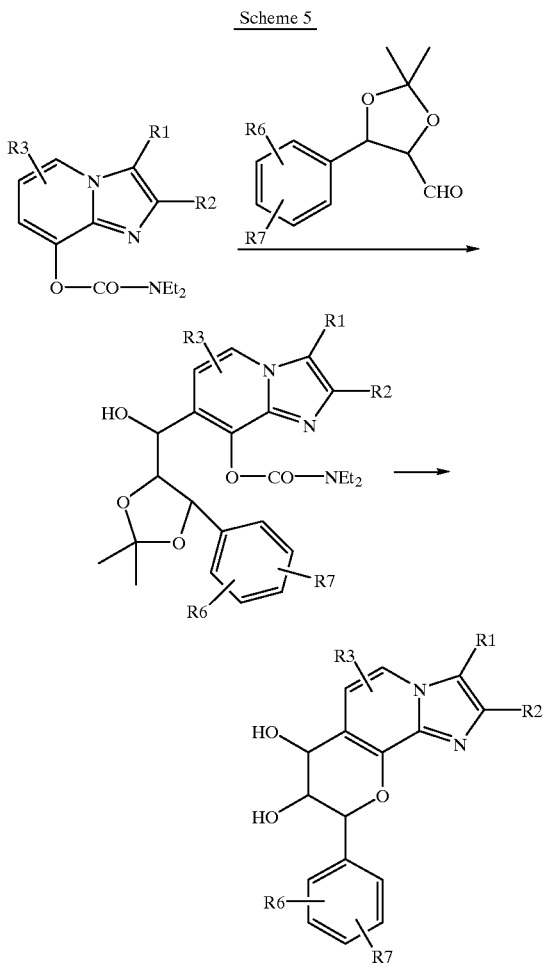

Scheme 5

The protected 8-hydroxyimidazo[2-a]pyridine known from Scheme 3 is deprotonated in the 7-position (e.g. with butyllithium) and reacted with protected aldehydes known from the literature. The removal of the protective group carried out under strongly acidic conditions (e.g. HBr in glacial acetic acid) yields the sought 7,8-dihydroxy compounds via a ring closure reaction, which for their part, if desired, can be converted into further compounds according to the invention, e.g. by (selective) alkylation or acylation of the hydroxyl groups.

In the above schemes, "R" is 1-4C alkyl, "Ac" is $CH_3CO$ and "Et" is $C_2H_5$.

Compounds of the formula I in which $R_4a/R_4b$ or $R_5a/R_5b$ are 1-4C-alkoxy, 1-4C-alkoxy-1-4C-alkoxy-1-4-C alkoxy or 1-4C-alkylcarbonyloxy can be prepared by customary derivatization measures, such as are familiar to the person skilled in the art (e.g. by alkylation or by acylation), from the corresponding compounds in which $R_4a/R_4b$ or $R_5a/R_5b$ are hydroxyl.

Compounds of the formula I in which $R_2$ is hydroxy-1-4C-alkyl or the corresponding starting compounds of the Schemes 1 to 5 can be, produced from the corresponding esters and aldehydes by reduction, for example with sodium borohydride or lithium aluminium hydride, in a customary manner (cf. WO 94/18199). If desired, the reduction for obtaining the hydroxy-1-4C-alkyl group can be accomplished simultaneously with the reduction of the keto group in position 8 and in particular in position 7 ($R_4a$ and $R_4b$ together are O).

The substances according to the invention are isolated and purified in a manner known per se, for example, by distilling off the solvent in vacuo and recrystallizing the residue obtained from a suitable solvent or subjecting it to one of the customary purification methods, such as, for example, column chromatography on suitable support material.

Salts are obtained by dissolving the free compound in a suitable solvent, e.g. in a chlorinated hydrocarbon, such as methyl chloride or chloroform, or a low molecular weight aliphatic alcohol (ethanol, isopropanol) which contains the desired acid, or to which the desired acid is subsequently added. The salts are obtained by filtering, reprecipitating, precipitating with a nonsolvent for the addition salt or by evaporating the solvent. Salts obtained can be converted by alkalization or by acidification into the free compounds, which in turn can be converted into salts. In this way, pharmacologically intolerable salts can be converted into pharmacologically tolerable salts.

The pure enantiomers, in particular the pure enantiomers of the formula I*, to which the invention preferably relates, can be obtained in a manner familiar to the person skilled in the art, for example by enantioselective synthesis, by chromatographic separation on chiral separating columns, by derivatization with chiral auxiliary reagents, subsequent separation of diastereomers and removal of the chiral auxiliary group, by salt formation with chiral acids, subsequent separation of the salts and liberation of the desired compound from the salt, or by (fractional) crystallization from a suitable solvent.

The invention further relates to the processes and the process intermediates described in the above schemes, in particular those process intermediates of Schemes 1, 2, 3, 4 and 5, which can be isolated before the cyclization step.

The following examples serve to illustrate the invention further without restricting it. Likewise, further compounds of the formula I whose preparation is not described explicitly can be prepared analogously or in a manner familiar to the person skilled in the art using customary process techniques. The abbreviation min stands for minute(s) and h for hour(s).

EXAMPLES

Final products 1. 8,9-cis-8-Hydroxy-2,3-dimethyl-9-phenyl-7H-8,9-dihydropyrano[2,3-c]imidazo[1,2-a]pyridine 4.3 g of 9-acetyloxy-8-bromo-2,3-dimethyl-9-phenyl-7H-8,9-dihydropyrano[2,3-c]imidazo[1,2-a]-pyridine are treated with 6.5 ml of tributyltin hydride and 0.1 g of 2,2'-azoisobutyronitrile in 80 ml of dry benzene and the mixture is refluxed for 2.5 h. After cooling to room temperature, it is treated with 10 ml of saturated potassium hydroxide solution in methanol and stirred at room temperature for 15 min. The solvent is then stripped off in vacuo and the residue which remains is purified twice on silica gel (eluent: methylene chloride/methanol=13/1). 1.0 g of the title compound of m.p. 248–249° C. is obtained after stirring in acetone.

2. 8,9-trans-8-Hydroxy-3-hydroxymethyl-2-methyl-9-phenyl-7H-8,9-dihydroprano[2,3-c]imidazo[1,2-a]pyridine 330 mg of (8,9)-trans-3-ethoxycarbonyl-8-hydroxy2-methyl-9-phenyl-7H-8,9-dihydropyrano[2,3-c]imidazo[1,2-a]pyridine are suspended in 30 ml of tetrahydrofuran, treated with 150 mg of lithium aluminum hydride and the mixture is heated to boiling. After refluxing for 1 hour, a further 50 mg of lithium aluminum hydride are added and the mixture is refluxed again for 6 hours. After cooling, 0.2 ml of water, 0.2 ml of 15% strength aqueous sodium hydroxide solution and a further 0.6 ml of water are slowly added successively, the resulting precipitate is filtered off, the filter cake is washed several times with methanol and the combined filtrate is chromatographed on silica gel after stripping off the solvent (eluent: methylene chloride/methanol=9/1). 280 mg of the title compound of m.p. 164–170° C. are obtained (ether/methanol).

3. 8.9-cis-8-Hydroxy-3-hydroxymethyl-2-methyl-9-phenyl-7H-8,9-dihydropyrano[2,3-c]imidazo[1,2-a]pyridine Analogously to Example 2, the title compound of m.p. 167° C (methanol) is obtained in 57% yield by reduction of (8,9)-cis-3-ethoxycarbonyl-8-hydroxy-2-methyl-9-phenyl-7H-8,9-dihydropyrano[2,3-c]imidazo[2-a]pyridine using lithium aluminum hydride.

4. 8,9-trans-3Hydroxymethyl-8-methoxy-2-methyl-9-phenyl-7H-8,9-dihydropyrano[2,3-c]imidazo[1,2-a]pyridine The title compound of m.p. 94–98° C. (2-propanol) is obtained in 75% yield by reduction of (8,9)-trans-3-ethoxycarbonyl-8-methoxy-2-methyl-9-phenyl-7H-8,9-dihydropyrano[2,3-c]imidazo[1,2-a]pyridine using lithium aluminum hydride analogously to the preparation of Example 2.

5. 8,9-cis-3-Hydroxymethyl-8-methoxy-2-methyl-9-phenyl-7H-8,9-dihydropyrano[2,3-c]imidazo[1,2-a] pyridine Analogously to Example 2, the title compound of m.p. 221–224° C. (acetone) is obtained in 70% yield by reduction of (8,9)-cis-3-ethoxycarbonyl-8-methoxy-2-methyl-9-phenyl-7H-8,9-dihydropyrano[2,3-c]imidazo[1,2-a]pyridine using lithium aluminum hydride.

6. 8,9-trans-8-Ethoxy-3-hydroxymethyl-2-methyl-9-phenyl-7H-8,9-dihydropyrano[2,3-c]imidazo[1,2-a]pyridine The title compound of m.p. 190–194° C. (diethyl ether) is obtained in 90% yield analogously to Example 2 by reduction of (8,9)-trans-8-ethoxy-3-ethoxycarbonyl-2-methyl-7H-8,9-dihydropyrano[2,3-c]imidazo[1,2-a]pyridine using lithium aluminium hydride.

7. 8-Hydroxy-7-oxo-9-phenyl-2,3-dimethyl-7H-8,9-dihydro-pyrano[2,3-c]imidazo[1,2-a]pyridine A suspension of 6 g of 8-(diethylaminocarbonyloxy)-2,3-dimethyl-7-(1-oxo-3-phenyl-2-propen-1-yl)-imidazo[2-a]pyridine in 120 ml of ethanol is cooled to 0° C., 15.3 ml of 2M aq. sodium hydroxide solution and 6 ml of 30% aq. hydrogenperoxide solution are added. After 8 h stirring the mixture is diluted with water, extracted twice with dichloromethane and the solvent is removed in vacuo. The remaining semisolid is purified on silica gel (eluent diethylacetat). The title compound of melting point 205–207° C. is obtained in 5% yield together with 15% 8-(diethylaminocarbonyloxy)-2,3-dimethyl-7-(2,3-epoxy-1-oxo-3-phenyl-prop-1-yl)-imidazo[1,2-a]pyridine.

8. 7,8-Dihydroxy-9-phenyl-2,3-dimethyl-7H-8,9-dihydro-pyrano[2,3-c]imidazo[1,2-a]pyridine To a suspension of 0.19 g of 8-hydroxy-7-oxo-9-phenyl-2,3-dimethyl-7H-8,9-dihydro-pyrano[2,3-c]imidazo[1,2-a]pyridine in 6 ml of methanol 0.06 g of sodium tetrahydridoboranate are added. After 1 h the solvent is removed in vacuo, 50 ml of water are added and the solution is extracted twice with trichloromethane (50 ml each). The combined organic solutions are dried over sodium sulfate, the solvent is stripped off in vacuo and the solid residue purified on silica gel (eluent dichloromethanelmethanol 13/1). The title compound of melting point 233–235° C. is obtained in 68% yield.

9. 7-Oxo-9-phenyl-2,3-dimethyl-7H-8,9-dihydro-pyrano[2,3-c]imidazo[1,2-a]pyridine A suspension of 2 g of 8-(diethylaminocarbonyloxy)-2,3-dimethyl-7-(1-hydroxy-3-phenyl-2-propen-1-yl)-imidazo[1,2-a]pyridine in 5 ml of a 33% solution of hydrogen bromide in acetic acid is heated for 1 h at 130° C. After stirring at room temperature for 48 h, the mixture is diluted with 50 ml of water and 50 ml of dichloromethane, neutralized with concentrated sodium hydroxide solution and extracted twice with dichloromethane. The combined organic solutions are washed, dried over sodium sulfate, the solvent is removed in vacuo and the residue purified on silica gel (eluent dichloromethanelmethanol 100/3 ). The title compound of melting point 174° C. (decomp.) is obtained in 80% yield.

10. 7-Hydroxy-9-phenyl-2,3-dimethyl-7H-8,9-dihydro-pyrano[2,3-c]imidazo[1,2-a]pyridine To a suspension of 0.6 g of 7-oxo-9-phenyl-2,3-dimethyl-7H-8,9-dihydro-pyrano[2,3-c]imidazo[1,2-a]pyridine in 10 ml of methanol 0.2 g of sodium tetrahydridoboranate is added in small portions. After 30 min stirring at room temperature the solvent is stripped off, 30 ml of water and 30 ml of dichloromethane are added, the organic layer is separated, the solvent removed in vacuo and the solid residue purified on silica gel (eluent dichloromethane/methanol 13/1). The title compound of melting point 204–205° C. (decomp.) is obtained in 93% yield.

Starting compounds 1.1 9-Acetyloxy-8-bromo-2,3-dimethyl-9-phenyl-7H-8,9-dihydropyrano[2,3-c]imidazo[1,2-a]pyridine 0.5 g of 2,3-dimethyl-9-phenyl-7H-pyrano[2,3-c]imidazo[1,2-a]pyridine is dissolved in a mixture of 10 ml of anhydrous acetic acid and 10 ml of acetic anhydride at room temperature, 0.4 g of bromosuccinimide is added by spatula, the mixture is stirred at room temperature for 0.5 h, the solvent is then stripped off in a high vacuum, the residue is taken up in 20 ml of methylene chloride, washed with saturated sodium hydrogencarbonate solution and then with water, the organic phase is dried over sodium sulfate and the solvent is removed in vacuo. The title compound is obtained in 93 % yield as a solid foam and used without further purification for the next step.

1.2 2,3-Dimethyl-9-phenyl-7H-pyrano[2,3-c]imidazo[1,2-a]pyridine

A solution of 8.8 g of 9-methoxy-9-phenyl-7H-8,9-dihydropyrano[2,3-c]imidazo[1,2-a]pyridine in 15 ml of dry chloroform is added dropwise under an argon atmosphere to a boiling solution of 11.8 g of p-toluenesulfonic acid and boiled in a water separator for 1 h. The solvent is then stripped off in vacuo, the residue which remains Is stirred with aqueous sodium hydrogencarbonate solution and methylene chloride, the organic phase is separated off and the aqueous phase Is extracted twice more with a little methylene chloride. The combined organic phases are washed with a little water, dried over sodium sulfate and the solvent is removed in vacuo. After purification on silica gel (eluent: methylene chloride/methanol=100/3), 3.3 g of the title compound of m.p. 120–123° C. are obtained.

1.3 9-Methoxy-2,3-dimethyl-9-phenyl-7H-8,9-dihydropyrano[2,3-c]imidazo[1,2-a]pyridine A mixture of 5.25 9 of 8-hydroxy-2,3-dimethyl-7-(3-phenyl-3-oxopropyl)-imidazo[1,2-a]pyridine, 22 ml of 2,2-dimethoxypropane and 100 ml of methylene chloride is treated at room temperature with 8.8 ml of commercially available boron trifluoride etherate solution and the mixture is stirred at room temperature for 16 h. 200 ml of a saturated sodium hydrogencarbonate solution are then added with vigorous stirring, the organic phase is separated off, extracted three times with a little methylene chloride, the combined organic phases are washed with a little water and dried over sodium sulfate, the solvent is stripped off in vacuo and the residue is treated with a little diisopropyl ether. The crystals which are deposited are filtered off, washed and dried in vacuo. 4.5 g of the title compound of m.p. 187–188° C. are obtained.

4,8-Hydroxy-2,3-dimethyl-7-(3-phenyl-3-oxopropyl)-imidazo[1,2-a]pyridine

The title compound of m.p. 157–160° C. (ethyl acetate) is prepared analogously to WO 95/27714.

2.1 (8,9)-trans-3-Ethoxycarbonyl-8-hydroxy-2-methyl-9-phenyl-7H-8,9-dihydropyrano[2,3-c]imidazo[1,2-a]pyridine 2 g of 3-ethoxycarbonyl-8-methoxy-7-(2,3-epoxy-3-phenylpropyl)-2-methylimidazo[1,2-a]pyridine are dissolved in 40 ml of methylene chloride at room temperature, cooled to -5° C, treated dropwise with 11 ml of a commercially available 1 molar boron tribromide solution in methylene chloride, the mixture is subsequently stirred for 2 hours, the solvent is stripped off in vacuo, and the residue is suspended in 50 ml of dioxane and treated with 12 ml of a saturated aqueous sodium hydrogencarbonate solution. The orange-colored suspension is stirred at room temperature for 16 hours, the solvent is stripped off in vacuo, the residue is taken up in water and extracted twice with methylene chloride, the combined organic phases are concentrated in vacuo and the residue is purified on silica get (eluent: methylene chloride/methanol=100/3).

0.27 g of the title compound of m.p. 173–175° C. (diethyl ether) is obtained.

2.2 3-Ethoxycarbonyl-8-methoxy7-(2,3-epoxy-3-phenyl-propyl)-2-methyl-imidazo[1,2-a]pyridine 4.2 g of -ethoxycarbonyl-8-methoxy-7-(2-bromo-3-oxo-3-phenylpropyl)-2-methyl-imidazo[1,2-a]pyridine are suspended in 42 ml of ethanol and treated at room temperature with 0.71 g of sodium borohydride. After stirring at room temperature for 2 hours, a further 90 mg of sodium borohydride are added, the mixture is concentrated to dryness in vacuo after stirring for a further 15 h, the residue is partitioned between 20 ml of a saturated ammonium chloride solution and 20 ml of methylene chloride, the methylene chloride phase is separated off and the aqueous phase is extracted three times with methylene chloride. The combined organic phases are washed with a little water, dried over sodium sulfate, and the solvent is stripped off in vacuo. The residue which remains is treated with diethyl ether and the crystals which are obtained in this process are filtered off.

2.05 g of the title compound of m.p. 97–98° C. are obtained.

2.3 3-Ethoxycarbonyl-8-methoxy-7-(2-bromo-3-oxo-3-phenylpropyl)-2-methyl-imidazo[1,2-a]pyridine 30.2 g of 3-ethoxycarbonyl-8-methoxy-2-methyl-7-(3-oxo-3-phenylpropyl)-imidazo[1,2-a]pyridine hydrobromide are dissolved in 600 ml of chloroform, treated dropwise in the course of 30 min with a solution of 3.83 ml of bromine in 40 ml of chloroform at room temperature, subsequently stirred for 18 hours, then washed with saturated sodium hydrogencarbonate solution, and the organic phase is then washed with water, dried over sodium sulfate and concentrated to dryness in vacuo. The residue is treated with a little diethyl ether and the crystals which are deposited are filtered off.

25.4 g of the title compound of m.p. 122–123° C. (diethyl ether) are obtained.

2.4 3-Ethoxycarbonyl-8-methoxy-2-methyl-7-(3-oxo-3-phenylpropyl)-imidazo[1,2-a]pyridine 57 g of finely ground potassium carbonate and 10.3 ml of methyl iodide are added successively to a suspension of 48.5 g of 3-ethoxycarbonyl-8-hydroxy-2-methyl-7-(3-oxo-3-phenylpropyl)imidazo[1,2-a]pyridine in 600 ml of dimethylformamide. The mixture is vigorously stirred at room temperature for 1.5 hours. Solid constituents are then filtered off, the filtrate is concentrated to dryness in a high vacuum and taken up in ethyl acetate, and the organic phase is washed with water. After drying over sodium sulfate, the solvent is stripped off in vacuo, the residue is treated with a little ethyl acetate and the crystals which are deposited are filtered off..

29.6 g of the title compound of m.p. 117–118° C. (ethyl acetate) are obtained.

3.1 (8,9)-cis-3-Ethoxycarbonyl-8-hydroxy-2-methyl-9-phenyl-7H-8,9-dihydropyrano[2,3-c]imidazo[1,2-a]pyridine 4.3 g of 3-ethoxycarbonyl-8-methoxy-7-(2,3-epoxy3-phenylpropyl)-2-methylimidazo[3,2-a]pyridine are treated dropwise in 80 ml of dichloromethane at −5° C. with 24 ml of a commercially available 1 molar solution of boron tribromide in methylene chloride (30 min), 100 ml of ice water are added after a further 30 min, the aqueous phase is adjusted to pH 6.5 using saturated sodium hydrogencarbonate solution and the organic phase is separated off. The aqueous phase is extracted three times with methylene chloride, the combined organic phases are washed with a little water and dried over sodium sulfate, and the solvent is stripped off in vacuo. The foamy residue is treated with 80 ml of ethanol and the mixture is refluxed for 6 hours. It is then concentrated to dryness in vacuo, stirred with aqueous sodium hydrogencarbonate solution and extracted three times with methylene chloride. The organic phases are combined, washed with a little water and dried over sodium sulfate, and the solvent is stripped off in vacuo. The residue which remains is chromatographed on silica gel (eluent: methylene chloride/methanol=100/2).

0.27 g of the title compound of m.p.>220° C. is obtained in addition to 1.73 g of the trans-compound of Example 2.1.

4.1 (8,9)-trans-3-Ethoxycarbonyl-8-methoxy-2-methyl-9-phenyl-7H-8,9-dihydropyrano[2,3-c]imidazo[1,2-a]pyridine 800 mg of (8,9)-trans-3-ethoxycarbonyl-8-hydroxy-2-methyl-9-phenyl-7H-8,9-dihydropyrano[2,3-c]-imidazo[1,2-a]pyridine are dissolved in 70 ml of tetrahydrofuran and treated with 450 mg of 80% strength sodium hydride. After stirring at room temperature for 20 min, 0.76 ml of methyl iodide is added. After a further 4.5 hours the mixture is cautiously poured onto a saturated ammonium chloride solution and extracted with ethyl acetate, the organic phase is dried over sodium sulfate and the solvent is stripped off in vacuo. The residue which remains is purified on silica gel (eluent: methylene chloride/methanol=13/1).

540 mg of the title compound of m.p. 153–155° C. (diethyl ether) are obtained.

5.1 (8,9)-cis-3-Ethoxycarbonyl-8-methoxy-2-methyl-9-phenyl-7H-8,9-dihydropyrano[2,3-c]imidazolyl[1,2-a]pyridine The title compound of m.p. 147–148° C. (acetone) is obtained in 90% yield analogously to Example 4.1 starting from the corresponding cis-compound.

6.1 (8,9)-trans-8-Ethoxy-3-ethoxy -2-methyl-7H-8,9-dihydropyrano[2,3-c]imidazo[1,2-a]pyridine The title compound of m.p. 164–166° C. (diethyl ether) is obtained in 54% yield analogously to Example 4.1 by ethylation of (8,9)-trans-3-ethoxycarbonyl-8-hydroxy-2-methyl-9-phenyl-7H-8,9-dihydropyrano[2,3-c]imidazo[1,2-a]pyridine with ethyl bromide.

7.1 8-(Diethylaminocarbonyloxy)-2,3-dimethyl-imidazo[1,2-a]pyridine

A mixture of 30 g of 8-hydroxy-2,3-dimethyl-imidazo[1,2-a]pyridine, 30 ml of diethylcarbamide chloride and 37.1 ml of triethylamine in 600 ml of toluene is refluxed for 20 h. After cooling the solution is washed twice with water (150 ml each), the solvent stripped off in vacuo, the solid residue washed twice with diethylether and acetone. The title compound of melting point 135–137° C. is obtained in 86% yield.

7.2 8-(Diethylaminocarbonyloxy)-2,3-dimethyl-7-(1-hydroxy-3-phenyl-2-propen-1-yl)-imidazo-[1,2-a]pyridine A solution of 5 g of 8-(diethylaminocarbonyloxy)-2,3-dimethyl-imidazo[1,2-a]pyridine in 50 ml of THF is cooled to −78° C., 23.6 ml of a 1.7 molar solution of t-butyllithium in pentane is added over a period of 5 min, and after additional 5 min stirring 5.1 ml of cinnamic aldehyde is added. The temperature of the mixture is then allowed to rise to ambient temperature, 300 ml of water and 300 ml of ethyl acetate is added, the organic layer separated, the solvent stripped off in vacuo and the remaining solid residue washed with diethylether and acetone. The title compound of melting point 190–192° C. is obtained in 65% yield.

7.3 8-(Diethylaminocarbonyloxy)-2,3-dimethyl-7-(1-oxo-3-phenyl-2-propen-1-yl)-imidazo-[1,2a]pyridine A mixture of 5.05 g of 8-(diethylaminocarbonyloxy)-2,3-dimethyl-7-(1-hydroxy-3-phenyl-2-propen-1-yl)-imidazo[1,2-a]pyridine and 9 g of manganese dioxide in 200 ml of trichloromethane is stirred for 36 h at room temperature, the solid is filtered off, the solvent removed in vacuo, and the solid residue washed with diethylether. The title compound of melting point 163–164° C. is obtained in 95% yield.

7.4 8-(Diethylaminocarbonyloxy)-2,3-dimethyl-7-(2,3-epoxy-1-oxo-3-phenyl-prop-1-yl)-imidazo-[1,2-a]pyridine A solution of 1 g of 8-(diethylaminocarbonyloxy)-2,3-dimethyl-7-(1-oxo-3-phenyl-2-propen-1-yl)-imidazo[1,2-a]pyridine in 40 ml of ethanol is cooled to −10° C. and a solution of 2.0 ml of aq. 30% hydroperoxide in 1.8 ml of 2M aq. sodium hydroxide solution is added. The mixture is stirred for 7 h at −10 to −5° C. and for 13 h at ambient temperature, extracted three times with dichloromethane (50 ml each), the solvent is removed in vacuo and the oily residue purified on silica gel (eluent diethyl acetate). The title compound is obtained in 15% yield as an amorphous solid.

Commercial Utility

The compounds of the formula I and their salts have useful pharmacological properties which make them commercially utilizable, in particular, they exhibit a marked inhibition of gastric acid secretion and an excellent gastric and intestinal protective action in warm-blooded animals, in particular humans. In this context, the compounds according to the invention are distinguished by a high selectivity of action, an advantageous duration of action, a particularly good enteral activity, the absence of significant side effects and a large therapeutic breadth.

"Gastric and intestinal protection" in this connection is understood as meaning the prevention and treatment of gastrointestinal diseases, in particular of gastrointestinal inflammatory diseases and lesions (such as, for example, stomach ulcers, duodenal ulcers, gastritis, hyperacidic or medicament-related functional gastropathy), which can be caused, for example, by microorganisms (e.g. Helicobacter pylori), bacterial toxins, medicaments (e.g. certain antiinflammatories and antirheumatics), chemicals (e.g. ethanol), gastric acid or stress situations.

In their excellent properties, the compounds according to the invention surprisingly prove to be clearly superior to the compounds known from the prior art in various models in which the antiulcerogenic and the antisecretory properties are determined. On account of these properties, the compounds of the formula I and their pharmacologically tolerable salts are outstandingly suitable for use in human and veterinary medicine, where they are used, in particular, for the treatment and/or prophylaxis of disorders of the stomach and/or intestine.

The invention therefore further relates to the compounds according to the invention for use in the treatment and/or prophylaxis of the abovementioned diseases.

The invention likewise comprises the use of the compounds according to the invention for the production of medicaments which are employed for the treatment and/or prophylaxis of the abovementioned diseases.

The invention furthermore comprises the use of the compounds according to the invention for the treatment and/or prophylaxis of the abovementioned diseases.

The invention furthermore relates to medicaments which contain one or more compounds of the formula I and/or their pharmacologically tolerable salts.

The medicaments are prepared by processes known per se, which are familiar to the person skilled in the art. As medicaments, the pharmacologically active compounds according to the invention (=active compounds) are employed either as such, or preferably in combination with suitable pharmaceutical auxiliaries or excipients in the form of tablets, coated tablets, capsules, suppositories, patches (e.g. as TTS), emulsions, suspensions or solutions, where the active compound content is advantageously between 0.1 and 95% and where, by the appropriate choice of the auxiliaries and excipients, a pharmaceutical administration form (e.g. a delayed-release form or an enteric form) exactly suited to the active compound and/or to the desired onset of action can be achieved.

The person skilled in the art is familiar, on the basis of his expert knowledge, with auxiliaries or excipients which are suitable for the desired pharmaceutical formulations. Beside solvents, gel-forming agents, suppository bases, tablet auxiliaries and other active compound carriers, it is possible to use, for example, antioxidants, dispersants, emulsifiers, antifoams, flavor corrigents, preservatives, solubilizers, colorants or, in particular, permeation promoters and complexing agents (e.g. cyclodextrins).

The active compounds can be administered orally, parenterally or percutaneously.

In general, it has proven advantageous in human medicine to ad minister the active compound(s) in the case of oral administration in a daily dose from approximately 0.01 to approximately 20, preferably 0.05 to 5, in particular 0.1 to 1.5, mg/kg of body weight, if appropriate in the form of several, preferably 1 to 4, individual doses to achieve the desired result. In the case of parenteral treatment, similar or (in particular in the case of intravenous administration of the active compounds), as a rule, lower doses can be used. The optimal dose and manner of ad ministration of the active compounds necessary in each case can easily be determined by any person skilled in the art on the basis of his expert knowledge.

If the compounds according to the invention and/or their salts are to be employed for the treatment of the abovementioned diseases, the pharmaceutical preparations can also contain one or more pharmacologically active constituents of other pharmaceutical groups. Examples which may be mentioned are: tranquilizers (for example from the benzodiazapines group, e.g. diazeparn), spasmolytics (e.g. bietamiverine or camylofin), anticholinergics (e.g. oxyphencyclimine or phencarbamide), local anesthetics (e.g. tetracaine or procaine), and, if appropriate, also enzymes, vitamins or amino.

To be emphasized in this connection, in particular, is the combination of the compounds according to the invention with pharmaceuticals which inhibit acid secretion, such as, for example, H2 blockers (e.g. cimetidine, ranitidine), H+/K+—ATPase inhibitors (e.g. omeprazole, pantoprazole), or furthermore with so-called peripheral anticholinergics (e.g. pirenzepine, telenzepine), and with gastrin antagonists with the aim of increasing the main action in an additive or superadditive sense and/or of eliminating or decreasing the side effects, or furthermore the combination with antibacterially active substances (e.g. cephalosporins, tetracyclines, penicillins, macrolides, nitrolmidazoles or alternatively bismuth salts) for the control of *Helicobacter pylori*. Antibacterially active combination components which may be mentioned are, for example, mezlocillin, ampicillin, amoxycillin, cefalothin, cefoxitin, cefotaxime, imipenem, gentamycin, amikacin, erythromycin, ciprofloxacin, metronidazole, clarithromycin, azithromycin and combinations thereof (e.g. clarithromycin+metronidazole).

Pharmacology

The excellent gastric protective action and the gastric acid secretion-inhibiting action of the compounds according to the invention can be demonstrated in animal experimental models. The compounds according to the invention investigated in the model mentioned below have been provided with numbers which correspond to the numbers of these compounds in the examples.

Testing of the secretion-inhibiting action on the perfused rat stomach

Table A below shows the effects of the compounds according to the invention on the pentagastrin-stimulated acid secretion of the perfused rat stomach in vivo after intravenous administration.

TABLE A

| No. | Dose ($\mu$mol/kg) i.v. | Inhibition of acid secretion (%) |
|---|---|---|
| 1 | 3 | 92 |
| 10 | 3 | 100 |

Methodology

The abdomen of anesthetized rats (CD rat, female, 200–250 g; 1.5 g/kg i.m. urethane) was opened after tracheotomy by means of a median upper abdominal incision and a PVC catheter was fixed transorally in the esophagus and another via the pylorus such that the ends of the tube just projected into the gastric lumen. The catheter leading from the pylorus led outwards into the right abdominal wall through a side opening.

After thorough rinsing (about 50–100 ml), warm physiological NaCl solution at 37° C. was continuously passed through the stomach (0.5 ml/min, pH 6.8–6.9; Braun-Unita I). The pH (pH meter 632, glass electrode EA 147;$\phi$=5 mm, Metrohm) and, by titration With a freshly prepared 0.01 N NaOH solution to pH 7 (Dosimat 665 Metrohm), the secreted HCl were determined in the effluent in each case collected at an interval of 15 minutes.

The gastric secretion was stimulated by continuous infusion of 1 $\mu$g/kg(=1.65 ml/h) of i.v. pentagastrin (left femoral vein) about 30 min after the end of the operation (i.e. after determination of 2 preliminary fractions). The substances to be tested were ad ministered intravenously in 1 ml/kg liquid volumes 60 min after the start of the pentagastrin continuous infusion.

The body temperature of the animals was kept at a constant 37.8–38° C. by infrared irradiation and heat pads (automatic, stepless control by means of a rectal temperature sensor).

What is claimed is:

1. A compound of formula I

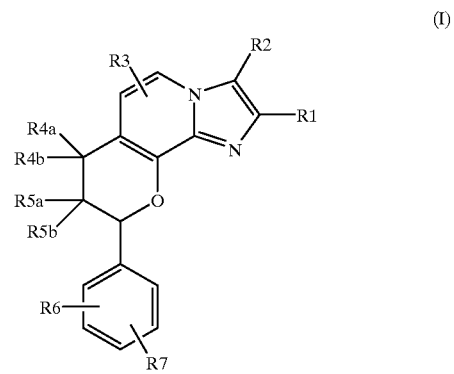

in which $R_1$ is 1-4C-alkyl, $R_2$ is 1-4C-alkyl or hydroxy-1-4C-alkyl, $R_3$ is hydrogen or halogen, one of the substituents $R_4a$ and $R_4b$ is hydrogen and the other is hydrogen, hydroxyl, 1-4C-alkoxy, 1-4C-alkoxy-1-4C-alkoxy or 1-4C-alkylcarbonyloxy, or in which $R_4a$ and $R_4b$ together are O (oxygen), one of the substituents $R_5a$ and $R_5b$ is hydrogen and the other is hydrogen, hydroxyl, 1-4C-alkoxy, 1-4C-alkoxy-1-4C-alkoxy or 1-4C-alkylcarbonyloxy, or in which $R_5a$ and $R_5b$ together are O (oxygen), where $R_4a$, $R_4b$, $R_5a$ and $R_5b$ are not simultaneously hydrogen, or in which one of the substituents $R_4a$ and $R_4b$ on the one hand and one of the substituents $R_5a$ and $R_5b$ on the other hand is in each case hydrogen, and the other substituents in each case together form a methylenedioxy radical (—O—CH$_2$—O—) or an ethylenedioxy radical (—O—CH$_2$—CH$_2$—O—), $R_6$ is hydrogen, halogen, 1-4C-alkyl, 1-4C-alkoxy, 1-4C-alkoxycarbonylamino, 1-4C-alkoxy-1-4C-alkoxycarbonylamino or trifluoromethyl and $R_7$ is hydrogen, halogen, 1-4C-alkyl or 1-4C-alkoxy, or a salt thereof.

2. A compound of formula I as claimed in claim 1, in which $R_1$ is 1-4C-alkyl, $R_2$ is 1-4C-alkyl or hydroxy-1-4C-alkyl, $R_3$ is hydrogen, one of the substituents $R_4a$ and $R_4b$ is hydrogen and the other is hydrogen, hydroxyl or 1-4C-alkoxy, or in which $R_4a$ and $R_4b$ together are O (oxygen), one of the substituents $R_5a$ and $R_5b$ is hydrogen and the other is hydrogen, hydroxyl or 1-4C-alkoxy, or in which $R_5a$ and $R_5b$ together are O (oxygen), where $R_4a$, $R_4b$, $R_5a$ and $R_5b$ are not simultaneously hydrogen, $R_6$ is hydrogen, halogen or trifluoromethyl and $R_7$ is hydrogen or halogen or a salt thereof.

3. Compounds as claimed in claim 1, which has the formula I*

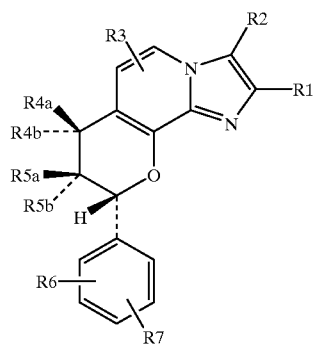

(I*)

in which $R_1$ is 1-4C-alkyl, $R_2$ is 1-C-alkyl or hydroxy-1-4C-alkyl, $R_3$ is hydrogen, one of the substituents $R_4a$ and $R_4b$ is hydrogen and the other is hydrogen, hydroxyl or 1-4C-alkoxy, one of the substituents $R_5a$ and $R_5b$ is hydrogen and the other is hydrogen, hydroxyl or 1-4C-alkoxy, where $R_4a$, $R_4b$, $R_5a$ and $R_5b$ are not simultaneously hydrogen, $R_6$ is hydrogen, halogen or trifluoromethyl and $R_7$ is hydrogen or halogen, or a salt thereof.

4. A compound of the formula I* as claimed in claim 3, in which $R_1$ is 1-4C-alkyl, $R_2$ is 1-4C-alkyl or hydroxymethyl, $R_3$ is hydrogen, $R_4a$ is hydrogen, $R_4b$ is hydroxyl or 1-4C-alkoxy, $R_5a$ is hydrogen, hydroxyl or 1-4C-alkoxy, $R_5b$ is hydrogen, $R_6$ is hydrogen, halogen or trifluoromethyl and $R_7$ is hydrogen or halogen, and their salts.

5. A compound of formula 1 as claimed in claim 3, in which $R_1$ is 1-4C-alkyl, $R_2$ is 1-4C-alkyl, $R_3$ is hydrogen, $R_4a$ is hydrogen, $R_4b$ is hydroxyl, $R_5a$ is hydroxyl, $R_5b$ is hydrogen, $R_6$ is hydrogen, halogen or trifluoromethyl and $R_7$ is hydrogen or halogen, or a salt thereof.

6. The compound as claimed in claim 1, selected from the group consisting of 8,9-trans-8-hydroxy-3-hydroxymethyl-2-methyl-9-phenyl-7H-8,9-dihydro-pyrano[2,3-c]imidazo[1,2-a]-pyridine, 8,9-cis-8-hydroxy-3-hydroxymethyl-2-methyl-9-phenyl-7H-8,9-dihydro-pyrano[2,3-c]imidazo[1,2-c]imidazo[12-a]pyridine, 8,9-trans-3-hydroxymethyl-8-methoxy-2-methyl-9-phenyl-7H-8,9-dihydro-pyrano-[2,3-c]imidazo[1,2-a] pyridine, 8,9-cis-3-hydroxymethyl-8-methoxy-2-methyl-9-phenyl-7H-8,9-dihydro-pyrano[2,3-c]imidazo[1,2-a]-pyridine, 8,9-trans-8ethoxy-3-hydroxymethyl-2-methyl-9-phenyl-7H-8,9-dihydropyrano[2,3-c]imidazo[1,2-a]-pyridine, 8-hydroxy-7-oxo-9-phenyl-2,3-dimethyl-7H-8,9-dihydro-pyrano[2,3-c]imidazo[1,2-a]pyridine, 7,8-dihydroxy-9-phenyl-2,3-dimethyl-7H-8,9-dihydro-pyrano[2,3-c]imidazo[1,2-a]pyridine, 7-oxo-9-phenyl-2,3-dimethyl-7H-8,9-dihydro-pyrano[2,3-c]imidazo[1,2-a]pyridine, 7-hydroxy-9-phenyl-2,3-dimethyl-7H -8,9-dihydro-pyrano[2,3-c]imidazo[2-a]pyridine, or a salt thereof.

7. The compound as claimed in claim 1 having the chemical name 8,9-cis-8-hydroxy-2,3-dimethyl-9-phenyl-7H-8,9-dihydropyrano[2,3-c]imidazo[1,2-a]pyridine, or a salt thereof.

8. A medicament composition comprising a compound as claimed in claim 1 and/or a pharmacologically tolerable salt thereof together with a customary pharmaceutical auxiliary and/or excipient.

9. A method of preventing or treating a gastrointestinal disease which comprises administering and effective amount of a compound as claimed in claim 1 or a pharmaceutically tolerable salt thereof to a warm-blooded animal subject to or afflicted with an amenable gastrointestinal disease.

10. A method of compounding a medicament composition which comprises an active ingredient for preventing or treating a gastrointestinal disease and a suitable pharmaceutical auxiliary and/or excipient, wherein the active ingredient is a compound as claimed in claim 1 or a pharmaceutically tolerable salt thereof.

* * * * *